(12) United States Patent
Freedman et al.

(10) Patent No.: US 11,866,689 B2
(45) Date of Patent: Jan. 9, 2024

(54) SPLICE-SWITCHING OLIGONUCLEOTIDES AND METHODS OF USE

(71) Applicant: Duke University, Durham, NC (US)

(72) Inventors: Jennifer Freedman, Durham, NC (US);
Steven Patierno, Durham, NC (US);
Daniel George, Durham, NC (US);
Bruce Sullenger, Durham, NC (US);
Bonnie LaCroix, Durham, NC (US);
Brendon Patierno, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 17/041,843

(22) PCT Filed: Mar. 22, 2019

(86) PCT No.: PCT/US2019/023670
§ 371 (c)(1),
(2) Date: Sep. 25, 2020

(87) PCT Pub. No.: WO2019/190927
PCT Pub. Date: Oct. 3, 2019

(65) Prior Publication Data
US 2021/0024932 A1    Jan. 28, 2021

Related U.S. Application Data

(60) Provisional application No. 62/647,897, filed on Mar. 26, 2018.

(51) Int. Cl.
| | | |
|---|---|---|
| *C07H 21/04* | (2006.01) | |
| *C12N 15/113* | (2010.01) | |
| *A61K 31/4166* | (2006.01) | |
| *A61K 31/712* | (2006.01) | |

(52) U.S. Cl.
CPC ........ *C12N 15/113* (2013.01); *A61K 31/4166* (2013.01); *A61K 31/712* (2013.01); *C12N 2310/315* (2013.01); *C12N 2310/321* (2013.01); *C12N 2310/3233* (2013.01); *C12N 2310/33* (2013.01)

(58) Field of Classification Search
None
See application file for complete search history.

(56) References Cited

U.S. PATENT DOCUMENTS

| | | | |
|---|---|---|---|
| 5,976,879 A | 11/1999 | Kole | |
| 2012/0283120 A1* | 11/2012 | Watanabe | C07K 14/721 435/6.12 |
| 2014/0107180 A1 | 4/2014 | MacLeod | |
| 2014/0206748 A1 | 7/2014 | Dehm | |

FOREIGN PATENT DOCUMENTS

| | | |
|---|---|---|
| EP | 2471918 A1 | 7/2012 |
| WO | 2017079570 A2 | 5/2017 |
| WO | 2018007475 A1 | 1/2018 |
| WO | 2020148400 A1 | 7/2020 |

OTHER PUBLICATIONS

Altschul, S. F., et al. "Basic local alignment search tool." Journal of molecular biology 215.3 (1990): 403-410.
Arnon, R. (Ed.) Synthetic Vaccines I: 83-92, CRC Press, Inc., Boca Raton, Fla., 1987.
Bauman, J.A., et al., Anti-tumor activity of splice-switching oligonucleotides. Nucleic Acids Res, 2010. 38(22): p. 8348-56.
Chono, S., et al., An efficient and low immunostimulatory nanoparticle formulation for systemic siRNA delivery to the tumor. J Control Release, 2008. 131(1): p. 64-9.
Flanagan, W. M., et al. "A cytosine analog that confers enhanced potency to antisense oligonucleotides." Proceedings of the National Academy of Sciences 96.7 (1999): 3513-3518.
Guo, Z., et al. "A novel androgen receptor splice variant is up-regulated during prostate cancer progression and promotes androgen depletion-resistant growth." Cancer research 69.6 (2009): 2305-2313.
Holmes, S. C., et al. "Steric inhibition of human immunodeficiency virus type-1 Tat-dependent trans-activation in vitro and in cells by oligonucleotides containing 2'-O-methyl G-clamp ribonucleoside analogues." Nucleic acids research 31.11 (2003): 2759-2768.
Hong, D., et al., AZD9150, a next-generation antisense oligonucleotide inhibitor of STAT3 with early evidence of clinical activity in lymphoma and lung cancer. Sci Transl Med, 2015. 7(314): p. 314ra185.
International Searching Authority. International Search Report and Written Opinion for application PCT/US2019/023670, dated Sep. 17, 2019. 12 pages.
Kole, R. et al, Exon skipping therapy for Duchenne muscular dystrophy. Adv Drug Deliv Rev, 2015. 87: p. 104-7.
Kotula, J.W., et al., Aptamer-mediated delivery of splice-switching oligonucleotides to the nuclei of cancer cells. Nucleic Acid Ther, 2012. 22(3): p. 187-95.
Lentz, J.J., et al., Rescue of hearing and vestibular function by antisense oligonucleotides in a mouse model of human deafness. Nat Med, 2013. 19(3): p. 345-50.
Li, S.D., et al, Efficient gene silencing in metastatic tumor by siRNA formulated in surface-modified nanoparticles. J Control Release, 2008. 126(1): p. 77-84.

(Continued)

*Primary Examiner* — Kimberly Chong
(74) *Attorney, Agent, or Firm* — Nutter McClennen & Fish LLP (57) ABSTRACT

The present disclosure provides methods and compositions for the treatment of cancer. In some aspects, the present disclosure provides splice-switching oligonucleotides that downregulate AR expression and methods of using these splice-switching oligonucleotides to treat cancer, specifically castrate resistant prostate cancer.

22 Claims, 4 Drawing Sheets
Specification includes a Sequence Listing.

(56) References Cited

OTHER PUBLICATIONS

Li, S.D., et al, Efficient oncogene silencing and metastasis inhibition via systemic delivery of siRNA. Mol Ther, 2008. 16(5): p. 942-6.
Roberts, J., et al., Efficient and persistent splice switching by systemically delivered LNA oligonucleotides in mice. Mol Ther, 2006. 14(4): p. 471-5.
Sazani, P., et al., Nuclear antisense effects of neutral, anionic and cationic oligonucleotide analogs. Nucleic Acids Res, 2001. 29(19): p. 3965-74.
Sazani, P., et al., Systemically delivered antisense oligomers upregulate gene expression in mouse tissues. Nat Biotechnol, 2002. 20(12): p. 1228-33.
Smith, T. F., et al. "Comparison of biosequences." Advances in applied mathematics 2.4 (1981): 482-489.
Sztainberg, Y., et al., Reversal of phenotypes in MECP2 duplication mice using genetic rescue or antisense oligonucleotides. Nature, 2015. 528(7580): p. 123-6.
Veedu, R.N. et al, Locked nucleic acids: promising nucleic acid analogs for therapeutic applications. Chem Biodivers, 2010. 7(3): p. 536-42.
Vo-Dinh, T., et al., SERS nanosensors and nanoreporters: golden opportunities in biomedical applications. Wiley Interdiscip Rev Nanomed Nanobiotechnol, 2015. 7(1): p. 17-33.
Yang, X., et al. "Novel membrane-associated androgen receptor splice variant potentiates proliferative and survival responses in prostate cancer cells." Journal of Biological Chemistry 286.41 (2011): 36152-36160.
Zanetta, C., et al., Molecular therapeutic strategies for spinal muscular atrophies: current and future clinical trials. Clin Ther, 2014. 36(1): p. 128-40.
Zhang, J. et al. "PowerBLAST: a new network BLAST application for interactive or automated sequence analysis and annotation." Genome research 7.6 (1997): 649-656.
Extended European Search Report for European Application No. 19776790.8, dated Nov. 29, 2021, 10 pages.
Luna Velez, M., et al., "Suppression of prostate tumor cell survival by antisense oligonucleotide-mediated inhibition of AR-V7 mRNA synthesis," Oncogene vol. 38, No. 19, 2019, pp. 3696-3709.
Ware, K., et al., "Biologic and Clinical Significance of Androgen Receptor Variants in Castration Resistant Prostate Cancer." Endocrine Related Cancer, vol. 21, No. 4, 2014, pp. T87-T103.

\* cited by examiner

SPLICE-SWITCHING OLIGONUCLEOTIDES AND METHODS OF USE

CROSS-REFERENCE TO RELATED APPLICATIONS

This patent application is a national stage filing under 35 U.S.C. 371 of International Application No. PCT/US2019/023670, filed Mar. 22, 2019, which claims priority to U.S. Provisional Application No. 62/647,897 filed Mar. 26, 2018, the contents of which are incorporated by reference in their entireties.

STATEMENT REGARDING FEDERALLY SPONSORED RESEARCH

N/A

BACKGROUND OF THE INVENTION

Prostate cancer is the second leading cause of cancer-related deaths in the US among men, with 174,650 new cases and 31,620 deaths estimated to occur in 2019. Previous work from our laboratory and others has revealed oncogenic signaling pathways contributing to aggressive disease, including androgen receptor (AR). The androgen receptor (AR) is a steroid hormone receptor that plays a crucial role in the development of normal prostate tissue, as well as in the progression of prostate cancer. Patients with metastatic disease are treated with androgen deprivation therapy.

African American (AA) men exhibit a nearly 2-fold higher incidence and 3-fold higher mortality rate from prostate cancer compared to white men and disparities in tumor aggressiveness remain after controlling for social determinants of health. Previous work from our laboratory and others has revealed differences in gene expression that contribute to prostate cancer health disparities among AAs. Oncogenic signaling pathways exhibiting up-regulation more often in prostate cancer in AA patients include androgen receptor (AR). Thus, novel therapeutic strategies capable of limiting aberrant constitutively active AR isoforms are urgently needed. Such strategies will increase our understanding of these molecular mechanisms underlying prostate cancer in AA men. In addition, such strategies provide novel specific approaches for treatment that will help reduce prostate cancer disparities for AAs and will improve treatment of advanced stage disease in all men with aggressive disease driven by these mechanisms.

SUMMARY OF THE INVENTION

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

One aspect of the disclosure provides anti-sense compound comprising, consisting essentially of, consisting of or is an optimized splice-switching oligonucleotide comprising, consisting essentially of, consisting of or is a sequence complementary to the region comprising a splice site of Exon CE3 of the androgen receptor (AR), more particularly a modified splice-switching oligonucleotide (SSO) consisting of 15 to 30 linked nucleosides and having a nucleobase sequence at least 80% complementary to the corresponding nucleotide sequence within SEQ ID NO:2 or SEQ ID NO:5 from a splice site of Exon CE3.

In another aspect, the anti-sense compound has a nucleobase sequence at least 80% complementary to the nucleotide sequence of SEQ ID NO:3.

the SSO consists of SEQ ID NO:1 (mC*mA*mG*mC*mC*mU*mU*mU*mC*mU*mU* mC*mA*mG*mG*mG*mU*mC), wherein m_* are nucleotides chemically modified to contain 2'-O-Me phosphorothioate backbones. [Arv7 Const]

In one aspect, the anti-sense compound comprises, consists essentially of, consists of or is an modified oligonucleotide comprises, consisting essentially of, consists of or is a sequence that is complementary to SEQ ID NO: 1. In some embodiments, SEQ ID NO:1 comprises the sequence mC*mA*mG*mC*mC*mU*mU*mU*mC*mU*mU*mC* mA*mG*mG*mG*mU*mC, wherein m_*=nucleotides are chemically modified, preferably are chemically modified to contain 2'-O-Me phosphorothioate backbones.

In another aspect, the disclosure provides an anti-sense compound which is a modified SSO having a nucleobase sequence at least 80% complementary to the corresponding nucleotide sequence of SEQ ID NO:5.

In another aspect, the disclosure provides an anti-sense compound of a SSO having a nucleobase sequence complementary to the nucleotide sequence selected from the group consisting of SEQ ID NO:6, SEQ ID NO:8, SEQ ID NO:10, SEQ ID NO:12, SEQ ID NO:14 and a sequence with at least 80% identity to SEQ ID NO:6, SEQ ID NO:8, SEQ ID NO:10, SEQ ID NO:12, or SEQ ID NO:14.

In another aspect, the disclosure provides an anti-sense compound consisting of a SSO with a sequence selected from the group consisting of SEQ ID NO:4 [ARv7 SSO-6], SEQ ID NO:7 [ARv7 SSO-6ext] and SEQ ID NO:9 [ARv7 SSO-6ext LN95mut], and a sequence with at least 80% identity to SEQ ID NO:4, SEQ ID NO:7 or SEQ ID NO:9, wherein each nucleoside of the SSO comprises a sugar modification.

In yet another aspect, the disclosure provides an anti-sense compound that is a SSO consisting of a nucleobase sequence at least 80% complementary to the nucleotide sequence selected from the group consisting of SEQ ID NO:12 [ARv7 morph 1], SEQ ID NO:14 [ARv7 morph 1 (LN95mut)] and a sequence with at least 80% identity to SEQ ID NO:12 or SEQ ID NO:14, and wherein each nucleosides is a morpholino oligomer.

In another aspect, the disclosure provides a method of treating a subject suffering from prostate cancer comprising administering to the subject a therapeutically effective amount of an anti-sense compound described herein or a composition comprising the anti-sense compound, wherein the prostate cancer is treated. In a preferred embodiment, the method comprises consists essentially of, or consists of administering to the subject a therapeutically effective amount of a composition comprising an anti-sense compound or splice-switching oligonucleotide as described herein and a second cancer therapy in an amount effective to treat the cancer as compared to the second cancer therapy alone.

In yet a further aspect, a kit for treating prostate cancer is provided. The kit comprises, consists essentially of, or consists of at least one anti-sense compound or modified SSO described herein. In some aspects, the kit further comprises a second cancer therapy, for example, an androgen therapy.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

The foregoing and other aspects and advantages of the present disclosure will appear from the following description.

DETAILED DESCRIPTION OF THE INVENTION

The present invention has been described in terms of one or more preferred embodiments, and it should be appreciated that many equivalents, alternatives, variations, and modifications, aside from those expressly stated, are possible and within the scope of the invention.

The present invention relates to methods, compounds and compositions for controlling expression of androgen receptor (AR) using anti-sense compounds that modulate splicing of pre-mRNA encoding this receptor. In a preferred embodiment, the compounds are splice-switching oligonucleotides or splice switching oligomers (SSOs).

Splice-switching oligonucleotides represent a novel therapeutic strategy to combat aggressive prostate cancer. Unlike standard RNA interference to inhibit the expression of a gene, SSOs simultaneously limit the production of pathogenic proteins and maintain/induce the expression of protein variants with therapeutic value. SSOs modulate pre-mRNA splicing by binding to target pre-mRNAs and blocking access of the splicing machinery to a particular splice site, and can be used to produce novel splice variants, correct aberrant splicing or manipulate alternative splicing.

The following terms are used herein:

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Unless otherwise defined, all technical terms used herein have the same meaning as commonly understood by one of ordinary skill in the art to which this disclosure belongs.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result. As used herein, "about" means within 5% of a stated numerical value.

The use herein of the terms "including," "comprising," or "having," and variations thereof, is meant to encompass the elements listed thereafter and equivalents thereof as well as additional elements. Embodiments recited as "including," "comprising/* or "having" certain elements are also contemplated as "consisting essentially of and "consisting of those certain elements.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

As used herein, "treatment" or "treating" refers to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. Specifically, treatment results in the reduction in tumor load or volume in the patient, and in some instances, leads to regression and elimination of the tumor or tumor cells, including a reduction in the number of tumor cells. As used herein, the term "treatment" is not necessarily meant to imply cure or complete abolition of the tumor. Treatment may refer to the inhibiting or slowing of the progression of the tumor, reducing the incidence of tumor, reducing the size of a tumor, reducing the number of tumor cells within a subject, reducing metastasis of the tumor, or preventing additional tumor growth. In some embodiments, treatment results in complete regression of the tumor.

By "ameliorate," "amelioration," "improvement" or the like we mean a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with the compositions of the present invention, where the untreated subjects have, or are subject to developing, the same or similar tumor.

The term "disease" as used herein includes, but is not limited to, any abnormal condition and/or disorder of a structure or a function that affects a part of an organism. It may be caused by an external factor, such as an infectious disease, or by internal dysfunctions, such as cancer, autoimmune diseases and the like. The preferred disease to be treated by the oligonucleotides, compositions and methods herein are diseases that results from or are associated with an increased expression of AR, for example, prostate cancer. In a specific embodiment, the disease is castrate resistant prostate cancer or prostate cancer that is or became resistant to androgen therapy.

As is known in the art, a "cancer" or "tumor" is generally considered as uncontrolled cell growth. The terms "cancer" and "tumor" are used herein interchangeably. The methods described herein may be used to treat a cancer which have an upregulation of androgen receptor (AR) associated with the cancer, for example, prostate cancer, more specifically castrate-resistant prostate cancer.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. Preferably, the subject is a human patient that is suffering from cancer (e.g., prostate cancer). In a preferred embodiment, the patient is suffering from an aggressive form of the cancer, for example an aggressive form of prostate cancer. In some embodiments, the patient is suffering from castrate-resistant prostate cancer. In some embodiments, the patient is a subject that has prostate cancer that is or has become resistant to androgen therapy.

As used herein, the term "altering the splicing of a pre-mRNA" refers to altering the splicing of a cellular pre-mRNA target resulting in an altered ratio of spliced products. Such an alteration of splicing can be detected by a variety of techniques well known to one of skill in the art. For example, RT-PCR can be used on total cellular RNA to detect the ratio of splice products in the presence and the absence of an SSO.

As used herein, the term "complementary" is used to indicate a sufficient degree of complementarity or precise pairing such that stable and specific binding occurs between an oligonucleotide and a DNA or RNA containing the target sequence. It is understood in the art that the sequence of an oligonucleotide need not be 100% complementary to that of its target. For example, for an SSO there is a sufficient degree of complementarity when, under conditions which permit splicing, binding to the target will occur and non-specific binding will be substantially avoided. Moreover, an oligonucleotide may hybridize over one or more segments such that intervening or adjacent segments are not involved in the hybridization event (e.g., a loop structure, mismatch or hairpin structure). The SSOs of the present invention comprise at least 70%, or at least 75%, or at least 80%, or at least 85%, or at least 90%, or at least 92%, or at least 95%, or at least 97%, or at least 98%, or at least 99%, or at least 100% sequence complementarity to a target region within the target nucleic acid sequence to which they are targeted. For example, a SSO in which 18 of 20 nucleobases of the SSO are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. Percent complementarity of a SSO with a region of a target nucleic acid can be determined routinely using BLAST programs (basic local alignment search tools) and Power-BLAST programs known in the art (Altschul et al., J. Mol. Biol., 1990, 215, 403-410; Zhang and Madden, Genome Res., 1997, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

As used here, a protein or nucleic acid has at least a specified percentage of sequence homology with a given SEQ ID NO, if the protein or nucleic acid in question has the same amino acid residues or bases, in the same sequence, in at least the specified percentage of residues or bases of the identified SEQ ID NO. In making nucleic acids with at least a given degree of sequence homology to a specified coding sequence, one skilled in the art, with the aid of a computer, could readily generate all nucleic acid sequences that would encode a given protein sequence. In making proteins with at least a given degree of sequence homology to specified protein sequence, one skilled in the art, guided by a knowledge of the physicochemical properties of amino acids, the position of a given residue within a protein, the known effects of certain amino acids on the conformation of proteins, and with the aid of a computer, could readily select certain amino acid substitutions at certain residue positions that would, with reasonable predictability, preserve the functional properties of the protein.

In one aspect, the disclosure provides an anti-sense compound comprising a modified splice-switching oligonucleotide (SSO) comprising, consisting essentially of, consisting of or is a sequence complementary to the region comprising a splice site of Exon CE3 of the androgen receptor (AR), particularly complementary to a region comprising, consisting essentially of, or consisting of SEQ ID NO: 2 or SEQ ID NO:5 In one embodiment, the anti-sense compound comprises a modified SSO consisting of 15 to 30 linked nucleosides having a nucleobase sequence at least 80% complementary to the corresponding nucleotide sequence within SEQ ID NO:2 or SEQ ID NO:5, alternatively at least 85% complementary to the corresponding nucleotide sequence within SEQ ID NO:2 or SEQ ID NO:5, alternatively at least 90% complementary to the corresponding nucleotide sequence of SEQ ID NO:2 or SEQ ID NO:5, alternatively at least 95% complementary to the corresponding nucleotide sequence of SEQ ID NO:2 or SEQ ID NO:5, alternatively at least 98% complementary to the corresponding nucleotide sequence of SEQ ID NO:2 or SEQ ID NO:5, alternatively at least 100% complementary to the corresponding region of the nucleotide sequence of SEQ ID NO:2 or SEQ ID NO:5.

Unless otherwise specified, the modified splice-switching oligonucleotide described herein specifically binds an RNA species encoded by an AR gene and/or encoding an AR polypeptide. The splice-switching oligonucleotides comprises or consists of 15 to 30 nuclesides, for example 15-25 nucleosides, for example 18 or 25 nucleosides.

In some embodiments, the modified SSO has a nucleobase sequence at least 80% complementary to the nucleotide sequence of SEQ ID NO:3, alternatively at least 85% complementary to the nucleotide sequence of SEQ ID NO:3, alternatively at least 90% complementary to the nucleotide sequence of SEQ ID NO:3, alternatively at least 95% complementary to the nucleotide sequence of SEQ ID NO:3, alternatively at least 98% complementary to the nucleotide sequence of SEQ ID NO:3. In some embodiments, the modified SSO is complementary to SEQ ID NO:3. For example, in one embodiment, a suitable SSO consists of SEQ ID NO:1 (mC*mA*mG*mC*mC*mU*mU*mU*mC*mU*mU*mC*mA*mG*mG*mG*mU*mC) (Arv7-Const1), wherein m_* are nucleotides chemically modified to contain 2'-O-Me phosphorothioate backbones. In one aspect, the modified SSO comprises, consisting essentially of, consists of or is a sequence with at least 80% identity to SEQ ID NO:1, more preferably at least 90% identity to SEQ ID NO:1, more preferably at least 95% identity to SEQ ID NO:1, alternatively 100% identity to SEQ ID NO:1. SEQ ID NO:1 comprises, consists essentially of, consists of, or is the sequence mC*mA*mG*mC*mC*mU*mU*mU*mC*mU*mU*mC*mA*mG*mG*mG*mU*mC (SEQ ID NO:1), wherein m_*=nucleotides are chemically modified, for example, modified to contain 2'-O-Me phosphorothioate backbones.

In another embodiment, the anti-sense compound or modified SSO described herein has a 15 to 30 nucleobase sequence at least 80% complementary to the corresponding nucleotide sequence of SEQ ID NO:5 (caacaatgtctctctttcat-actagAAAAATTCCGGGTTGGCAATTGCAA). For example, the anti-sense compound consists of a modified SSO has a nucleobase sequence at least 80% complementary to the nucleotide sequence selected from the group consisting of SEQ ID NO:6, SEQ ID NO:8, SEQ ID NO:10, SEQ ID NO:12 and SEQ ID NO:14, alternatively a nucleobase sequence at least 90% complementary to the nucleotide sequence selected from the group consisting of SEQ ID NO:6, SEQ ID NO:8, SEQ ID NO:10, SEQ ID NO:12, and SEQ ID NO:14, alternatively at least 95% complementary to the nucleotide sequence selected from the group consisting of SEQ ID NO:6, SEQ ID NO:8, SEQ ID NO:10, SEQ ID NO:12, alternatively the SSO has a nucleobase sequence complementary to the nucleotide sequence selected from the group consisting of SEQ ID NO:6, SEQ ID NO:8, SEQ ID NO:10, SEQ ID NO:12, SEQ ID NO:14.

For example, suitable anti-sense compound or modified SSO consists of a sequence selected from the group consisting of SEQ ID NO:1 [ARv7 Const1], SEQ ID NO:4 [ARv7 SSO-6], SEQ ID NO:7 [ARv7 SSO-6ext] and SEQ ID NO:9 [ARv7 SSO-6ext LN95mut], and a sequence with at least 80% identity to SEQ ID NO:1, SEQ ID NO:4, SEQ ID NO:7 or SEQ ID NO:9, wherein each nucleoside of the SSO comprises a modification, for example a backbone modification or sugar modification.

In one embodiment, a suitable example of an anti-sense compound or modified SSO that is complementary to SEQ ID NO:6 is an SSO having a nucleoside sequence of SEQ ID NO:4 [ARv7 SSO-6] or a sequence with at least 80% identity to SEQ ID NO:4.

In one embodiment, a suitable example of an anti-sense compound or modified SSO that is complementary to SEQ ID NO:8 is an SSO having a nucleoside sequence of SEQ ID NO:7 [ARv7 SSO-6ext] or a sequence with at least 80% identity to SEQ ID NO:7.

In one embodiment, a suitable example of an anti-sense compound or modified SSO that is complementary to SEQ ID NO:10 is an SSO having a nucleoside sequence of SEQ ID NO:9 [ARv7 SSO-6ext-NM95mut] or a sequence with at least 80% identity to SEQ ID NO:9.

In a preferred embodiment, the modified SSOs have been modified with a 2'-O-Me phosphorothioate backbone.

In another embodiment, the modified SSO of the present disclosure are Morpholinos. For example, in one embodiment, the anti-sense compound or modified SSO consists of a nucleobase sequence complementary to the nucleotide sequence selected from the group consisting of SEQ ID NO:12 (ARv7 morph 1), SEQ ID NO:14 (ARv7 morph 1 (LN95mut)) and a sequence with at least 80% identity to SEQ ID NO:12 or SEQ ID NO:14, and wherein each nucleosides is a Morpholino oligomer. As demonstrated in the examples, the Morpholinos reduce the ARv7 splice variant when introduced into prostate cancer cells.

Suitable Morpholino oligomers of the present disclosure include a modified SSO comprising, consisting essentially of, consisting of a sequence selected from the group consisting of SEQ ID NO:11, SEQ ID NO:13, and a sequence with at least 80% identity to SEQ ID NO:11 or SEQ ID NO:13, alternatively at least 85% identity to SEQ ID NO:11 or SEQ ID NO:13, alternatively at least 90% identity to SEQ ID NO:11 or SEQ ID NO:13, alternatively at least 95% identity to SEQ ID NO:11 or SEQ ID NO:13, alternatively at least 98% identity to SEQ ID NO:11 or SEQ ID NO:13, alternatively 100% identity to SEQ ID NO:11 or SEQ ID NO:13, wherein each nucleoside is a morpholino oligomer.

The modified SSOs described herein are modified in at least one way from the naturally occurring nucleotides to which they can anneal, more particularly the SSOs are modified by having a non-natural backbone or non-naturally occurring internucleoside linkages. The modified SSOs described herein can be several chemistries that hybridize to RNA, but that do not activate the destruction of the target RNA by RNase H, as do conventional antisense 2'-deoxy oligonucleotides. These oligonucleotides may contain modified, e.g. non-naturally occurring internucleoside linkages. For example, in some embodiments, the oligonucleotides have one or more modified internucleoside linkages. The modified splice-switching oligonucleotides in one embodiment comprise one or more modified nucleotides, such as a locked nucleic acid (LNA) or methylated nucleotides. LNA, often referred to as inaccessible RNA, is a modified RNA nucleotide. The ribose moiety of an LNA nucleotide is modified with an extra bridge connecting the 2' oxygen and 4' carbon. The invention can be practiced using 2'O modified nucleic acid oligomers, such as where the 2'O is replaced with —O—CH3, —O—CH2-CH2-O—CH3, —O—CH2-CH2-CH2-NH2, —O—CH2-CH2-CH2-OH or —F, where 2'O-methyl (2'-OMe) or 2'O-methyloxyethyl (MOE) is preferred. The nucleobases do not need to be linked to sugars, for example, as is the case of using Morpholino oligomers.

A number of chemical modifications increase binding affinity, stability and delivery of oligonucleotides to cells and tissues and can be used in the practice of the current invention. Oligonucleotides containing 2'-O-Me phosphorothioate backbones have been used by our collaborators to correct aberrant splicing of modified luciferase pre-mRNA (Kotula, J. W., et al., Aptamer-mediated delivery of splice-switching oligonucleotides to the nuclei of cancer cells. Nucleic Acid Ther, 2012. 22(3): p. 187-95) and by others to correct splicing of USH1C and rescue hearing and vestibular function (Lentz, J. J., et al., Rescue of hearing and vestibular function by antisense oligonucleotides in a mouse model of human deafness. Nat Med, 2013. 19(3): p. 345-50). Additional studies have shown efficacy and, in some cases, superior efficacy of oligonucleotides containing other types of chemically modified backbones. For example, correction of splicing of modified enhanced green fluorescent protein pre-mRNA by oligonucleotides containing morpholino, peptide nucleic acid, locked nucleic acid and 2☐-O-(2-methoxyethyl) modified backbones (Sazani, P., et al., Nuclear antisense effects of neutral, anionic and cationic oligonucleotide analogs. Nucleic Acids Res, 2001. 29(19): p. 3965-74; Roberts, J., et al., Efficient and persistent splice switching by systemically delivered LNA oligonucleotides in mice. Mol Ther, 2006. 14(4): p. 471-5; Sazani, P., et al., Systemically delivered antisense oligomers upregulate gene expression in mouse tissues. Nat Biotechnol, 2002. 20(12): p. 1228-33; Veedu, R. N. and J. Wengel, Locked nucleic acids: promising nucleic acid analogs for therapeutic applications. Chem Biodivers, 2010. 7(3): p. 536-42, the contents of which are incorporated by reference in their entireties), decrease of STAT3 and antitumor activity in lymphoma and lung cancer as well as in patients in a Phase I dose escalation study by oligonucleotides containing 2'-O-(2-methoxyethyl) modified backbones (Hong, D., et al., AZD9150, a next-generation antisense oligonucleotide inhibitor of STAT3 with early evidence of clinical activity in lymphoma and lung cancer. Sci Transl Med, 2015. 7(314): p. 314ra185) and reduction of methyl-CpG-binding protein 2 (MeCP2) to rescue MECP2 duplication syndrome and correct MECP2 levels in cells from MECP2 duplication patients by oligonucleotides containing 2'-O-(2-methoxyethyl) modified backbones (Sztainberg, Y., et al., Reversal of phenotypes in MECP2 duplication mice using genetic rescue or antisense oligonucleotides. Nature, 2015. 528(7580): p. 123-6).

It will be obvious to one skilled in the art that additional oligomer chemistries can be used to practice the invention including phosphorodiamidate-linked morpholino oligomers (PMO) or locked nucleic acid (LNA) oligomers.

In one embodiment, the SSOs are Morpholinos, Morpholino oligomers or phosphorodiamidate-linked morpholino oligomers (PMO), the terms of which are used interchangeably. A Morpholinos are synthetic molecules of a DNA bases attached to a backbone of methylenemorpholine rings linked through phosphorodiamidate groups. In some embodiments, the morpholino oligomers are about 25 bases in length (e.g., from about 15-30 bases) and bind to complementary sequences of RNA or single-stranded DNA by standard nucleic acid base-pairing. While Morpholinos have standard nucleic acid bases, those bases are bound to methylenemorpholine rings linked through phosphorodiamidate groups instead of phosphates found in DNA and RNA. Since Morpholinos contain uncharged phosphorodiamidate groups, Morpholinos in organisms or cells are uncharged molecules. The entire backbone of a Morpholino is made from these modified subunits.

The SSOs of this invention can be made through the well-known technique of solid phase synthesis. Any other means for such synthesis known in the art can additionally or alternatively be used. It is well known to use similar techniques to prepare oligonucleotides such as the phosphorothioates and alkylated derivatives. Suitable SSOs can also be ordered from suitable oligomer companies, for example Bio Basic (biobasic.com) which can provide SSOs containing chemically modified 2'-O-Me phosphorothioate backbones.

The bases of the SSO can be the conventional cytosine, guanine, adenine and uracil or thymidine bases. Alternatively, modified bases can be used. Of particular interest are modified bases that increase binding affinity. One non-limiting example of preferred modified bases are the so-called G-clamp or 9-(aminoethoxy)phenoxazine nucleotides, cytosine analogues that form 4 hydrogen bonds with guanosine. (Flanagan, W. M., et al., 1999, Proc. Natl. Acad. Sci. 96:3513; Holmes, S. C., 2003, Nucleic Acids Res. 31:2759). Specific examples of other bases include, but are not limited to, 5-methylcytosine (MeC), isocytosine, pseudoisocytosine. 5-(1-propynyl)-cytosine, 5-bromouracil, 5-(1-propynyl)-uracil, 5-propyny-6,5-methylthiazoleuracil, 6-aminopurine, 2-aminopurine, inosine, 2,6-diaminopurine, 7-propyne-7-deazaadenine, 7-propyne-7-deazaguanine and 2-chloro-6-aminopurine.

In one embodiment, an SSO (AR-V7 SSO) reduces splicing of the AR pre-mRNA to AR-V7 (the constitutively active truncated AR) and maintains splicing of the wildtype AR. In a preferred embodiment, the AR-V7 SSO comprises, consists essentially of or is SEQ ID NO:3, SEQ ID NO:4, SEQ ID NO:7, SEQ ID NO:9, SEQ ID NO:11 or SEQ ID NO:13.

Compositions comprising the anti-sense compounds described herein are also contemplated. Suitably, the composition comprises the anti-sense compound and a pharmaceutically acceptable carrier. Pharmaceutically acceptable carriers are well known to those of ordinary skill in the art (Arnon, R. (Ed.) Synthetic Vaccines 1:83-92, CRC Press, Inc., Boca Raton, Fla., 1987). They include liquid media suitable for use as vehicles to introduce the splice-switching oligonucleotides into a subject. In a preferred embodiment, the pharmaceutically acceptable carrier is a carrier that retains the stability of the SSO, and does not degrade the SSO during storage or treatment.

In a preferred embodiment, the SSO's are stored in a lyophilized product until use. In other embodiments, SSOs can be resuspended in nuclease free water and stored.

Compositions of the present invention may comprise sterile aqueous and nonaqueous injection solutions of the SSOs, which preparations are preferably isotonic with the blood of the intended subject and essentially pyrogen free. These preparations may contain anti-oxidants, buffers, bacteriostats, and solutes which render the formulation isotonic with the blood of the intended subject. Aqueous and nonaqueous sterile suspensions can include, but are not limited to, suspending agents and thickening agents. The formulations may be presented in unit dose or multi-dose containers, for example, sealed ampoules and vials, and may be stored in freeze-dried (lyophilized) condition requiring only the addition of the sterile liquid carrier, for example, saline or water-for-injection immediately prior to use.

In some embodiments, the compositions of the SSOs may be contained within a lipid particle or vesicle, such as a liposome or microcrystal, which may be suitable for parenteral administration. The particles may be of any suitable structure, such as unilamellar or plurilameller, so long as the SSOs are contained therein. Positively charged lipids such as N-[1-(2,3-dioleoyloxi)propyl]-N,N,N-trimethyl-ammoniummethylsulfate, or "DOTAP," are particularly preferred for such particles and vesicles. The preparation of such lipid particles is well known. [See references in U.S. Pat. No. 5,976,879 col. 6, incorporated by reference in its entirety]. Methods of delivery of SSOs using nanoparticles can be found in Huang et al. and Chono et al. and have been successfully utilized by Bauman et al. to deliver the SSO redirecting splicing of the Bcl-x pre-mRNA to a murine melanoma tumor model (See, e.g. Bauman, J. A., et al., *Anti-tumor activity of splice-switching oligonucleotides.* Nucleic Acids Res, 2010. 38(22): p. 8348-56; Li, S. D., S. Chono, and L. Huang, Efficient oncogene silencing and metastasis inhibition via systemic delivery of siRNA. Mol Ther, 2008. 16(5): p. 942-6; and Li, S. D., S. Chono, and L. Huang, Efficient gene silencing in metastatic tumor by siRNA formulated in surface-modified nanoparticles. J Control Release, 2008. 126(1): p. 77-84, Chono, S., et al., An efficient and low immunostimulatory nanoparticle formulation for systemic siRNA delivery to the tumor. J Control Release, 2008. 131(1): p. 64-9, which are incorporated by reference in their entireties). Methods whereby bodily fluids, organs or tissues are contacted with an effective amount of one or more of the splice-switching oligonucleotides or compositions of the invention are also contemplated. Bodily fluids, organs or tissues can be contacted with one or more of the splice-switching oligonucleotides of the invention resulting in modulation of AR expression in the cells of bodily fluids, organs or tissues. An effective amount can be determined by monitoring the modulatory effect of the splice-switching oligonucleotides or compositions on target nucleic acids or their products by methods routine to the skilled artisan.

The present invention provides for the use of SSOs described above for the preparation of a medicament for controlling the alternative splicing of androgen receptor (AR), specifically for reducing the expression of AR in tumor cells, more particularly prostate cancer cells. In the manufacture of a medicament according to the invention, the SSOs are typically admixed with, inter alia, an acceptable carrier. The carrier must be acceptable in the sense of being compatible with any other ingredients in the composition and must not be deleterious to the patient. The carrier may be a solid or liquid.

The anti-sense compounds, modified SSO and compositions described herein can be used to control the alternative splicing of AR so that there is reduction of the expression of AR in prostate cancer.

In another embodiment, the disclosure provides a method of treating a subject suffering from prostate cancer comprising administering to the subject a therapeutically effective amount of anti-sense compound, modified SSO or composition described herein to treat the cancer.

Suitable subjects for treatment include a subject having prostate cancer, more particularly a subject having prostate cancer that is non-responsive to androgen therapy or is castrate-resistant prostate cancer. In some embodiments, the subject is an African American male suffering from prostate cancer.

In some embodiments, the method further comprises administering to the subject a second cancer therapy. The combination of the SSOs and the second cancer therapy results in an increase in the efficacy of the treatment of the cancer than the second therapy administered alone. Suitable second cancer therapies are known in the art and include, but are not limited to, for example, chemotherapy, hormone therapy, androgen therapy, radiation, surgery, vaccine therapy and combinations thereof. In a preferred embodiment, the secondary cancer therapy is an androgen therapy, for example, an antiandrogen therapy.

Androgen therapy or Androgen deprivation therapies (ADT) are therapies that reduce the levels of androgen hormones, or interfere with androgen receptor function/signaling, for example by use of androgen receptor-pathway targeting (e.g. antiandrogens) or chemical castration. Suitable ADT therapies are known to one skilled in the art and include, but are not limited to, luteinizing hormone-releasing hormone (LHRH, or gonadotropin-releasing hormone (GnRH)) analogues (agonists), LHRH or GnRH antagonists, AR antagonists, androgen synthesis inhibitors, other AR degrading or blocking agents, and combinations thereof. Suitable ADT include treatment with one or more of the following:

(a) AR antagonists, including, but not limited to, flutamide, nilutamide, bicalutamide, enzalutamide, apalutamide, cyproterone acetate, megestrol acetate, chlormadinone acetate, spironolactone, canrenone, drospirenone, topilutamide (fluridil), cimetidine;

(b) androgen synthesis inhibitors, including, but not limited to, (i) 5a-reductase inhibitors, which include the non-limiting examples of finasteride, dutasteride, alfatradiol, and saw palmetto extract, (ii) CYP17A1 (17a-hydroxylase, 17,20-lyase) inhibitors, which include the non-limiting examples cyproterone acetate, spironolactone, danazol, gestrinone, ketoconazole, abiraterone acetate; (iii) 3 β-Hydroxy steroid dehydrogenase inhibitors, which include the non-limiting examples danazol, gestrinone, abiraterone acetate; (iv) 17P-Hydroxy steroid dehydrogenase inhibitors, which include the non-limiting examples danazol, simvastatin; (v) CYPl lAl (cholesterol side-chain cleavage enzyme) inhibitors, which include the non-limiting examples aminoglutethimide, danazol; and (vi) HMG-CoA reductase inhibitors, which include the non-limiting example statins (e.g., atorvastatin, simvastatin);

(c) antigonadotropins including (i) progestogens, such as the non-limiting examples including progesterone, cyproterone acetate, medroxyprogesterone acetate, megestrol acetate, chlormadinone acetate, spironolactone, drospirenone; (ii) estrogens including the non-limiting examples of estradiol, ethinyl estradiol, diethylstilbestrol, conjugated equine estrogens; (iii) GnRH analogues, for example, GnRH agonists, including non-limiting examples buserelin, deslorelin, gonadorelin, goserelin, histrelin, leuprorelin, nafarelin, triptorelin; GnRH antagonists, including non-limiting examples abarelix, cetrorelix, degarelix, ganirelix; and combinations thereof. For example, suitable ADT treatment include, but are not limited to, AR antagonists bicalutamide (Casodex, AstraZeneca®), apalutamide (ARN-509, Janssen), or enzalutamide (Xtandi, Astellas®), GnRH antagonist degarelix (Firmagon, Ferring Pharmaceuticals®), AR degrading agents such as galeterone (Tokai) and the like.

In a preferred embodiment, the androgen therapy is enzalutamide.

In some embodiments, the anti-sense compounds described herein can increase the susceptibility of a castrate-resistant prostate cancer cell to androgen therapy, for example, can increase the ability of an androgen therapy to provide a therapeutic effect in such a patient. In some embodiments, the anti-sense compounds described herein are able to increase the efficacy of an androgen therapy against prostate cancer cells.

In some embodiments, the anti-sense compounds, SSOs and compositions described herein can resensitize a cancer cell (e.g., prostate cancer cell) to androgen therapy. For example, in some embodiment, a method of treating an androgen therapy resistant cancer is provided. The method comprises administering the anti-sense compounds, SSOs and compositions described herein in combination with one or more androgen therapies (e.g., ADT), wherein the anti-sense compounds, SSOs and compositions is administered in an amount effective to resensitize a cancer cell to the androgen therapy.

Clinical studies and associated delivery options for SSOs that can be used in the practice of the invention can be found in for example, Kole, R. and A. M. Krieg, *Exon skipping therapy for Duchenne muscular dystrophy*. Adv Drug Deliv Rev, 2015. 87: p. 104-7; Zanetta, C., et al., Molecular therapeutic strategies for spinal muscular atrophies: current and future clinical trials. Clin Ther, 2014. 36(1): p. 128-40; and Hong, D., et al., AZD9150, a next-generation antisense oligonucleotide inhibitor of STAT3 with early evidence of clinical activity in lymphoma and lung cancer. Sci Transl Med, 2015. 7(314): p. 314ra185, the contents of which are incorporated by reference in their entireties.

Methods for reducing the expression of AR in a cancer cell are also provided. The method comprises treating the cancer cell with an SSO described herein. Cells can be transfected with SSOs in Opti-MEM medium, and cells can be cultured in medium known in the art, for example, medium containing LNCaP, H520, A549, 22RV1: phenol red-free RPMI 1640+10% FBS; LN95: phenol red-free RPMI+10% charcoal stripped FBS; PC3, VCaP: DMEM+ 10% FBS; MDA PCa 2b: F12-K+20% FBS+25 ng/mL cholera toxin+10 ng/mL EGF+0.005 mM phosphoethanolamine+100 pg/mL hydrocortisone+45 nM selenious acid+0.005 mg/mL insulin, and the like. In some embodiments, the cancer cell is in a subject suffering from the cancer.

In one embodiment, the SSO of the invention inhibits the expression of AR causing a reduction of RNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% in at least one cell.

In some embodiments, the SSOs may be delivered via aptomers, Inverse Molecular Sentinel nanoprobes, SSO encapsulated liposome-DNA-polycation or SSO encapsulated liposome-protamine-hyluronic acid nanoparticles and the like. Suitable methods of delivering aptamers can be found in Kotula, J. W., et al., Aptamer-mediated delivery of splice-switching oligonucleotides to the nuclei of cancer cells. Nucleic Acid Ther, 2012. 22(3): p. 187-95, the contents of which are incorporated by reference in their entirety. SSOs can be delivered to prostate cancer cells using Inverse Molecular Sentinel nanoprobes, methods of making can be found in Vo-Dinh, T., et al., *SERS nanosensors and nanoreporters: golden opportunities in biomedical applications*. Wiley Interdiscip Rev Nanomed Nanobiotechnol, 2015. 7(1): p. 17-33, which are incorporated by reference in their entirety.

Methods of delivering Morpholinos are known in the art, including, but not limited to, attaching or covalently linking the Morpholinos with chemical moieties that improve uptake of the oligos by cells. For example, Morpholinos may be attached to cell penetrating peptides (CPP). Other methods are understood by one skilled in the art.

Aspects of the present disclosure that are described with respect to methods can be utilized in the context of the pharmaceutical compositions or kits discussed in this disclosure. Similarly, aspects of the present disclosure that are described with respect to the pharmaceutical compositions can be utilized in the context of the methods and kits, and aspects of the present disclosure that are described with respect to kits can be utilized in the context of the methods and compositions.

This disclosure provides kits. The kits can be suitable for use in the methods described herein. Suitable kits include a kit for treating prostate cancer comprising an anti-sense compound, modified SSO or composition comprising at least one SSO described herein. In one aspect, the kit provides pharmaceutical composition comprising SSOs in amounts effective for treating cancer, more preferably prostate cancer. In some aspects, the kits provides a composition comprising at least one SSO and at least one second cancer therapy. In some aspects, instructions on how to administer the composition and/or SSOs.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present invention is well adapted to carry out the objects and obtain the ends and advantages mentioned, as well as those inherent therein. The present disclosure described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The following non-limiting examples are included for purposes of illustration only, and are not intended to limit the scope of the range of techniques and protocols in which the compositions and methods of the present invention may find utility, as will be appreciated by one of skill in the art and can be readily implemented.

EXAMPLES

Example 1: SSOs to Alter Splice Variants of AR

Herein we have designed and synthesized novel optimized SSOs targeting AR pre-mRNAs to correct aberrant splicing as follows. We have synthesized a SSO to correct the aberrant splicing that leads to production of the constitutively active AR-V7 variant. Transfection of prostate cancer cells with this chemically modified SSO, which targets the splice site of the cryptic exon included in AR-V7, decreases AR-V7 RNA and protein and proliferation of cells.

Figure 1:
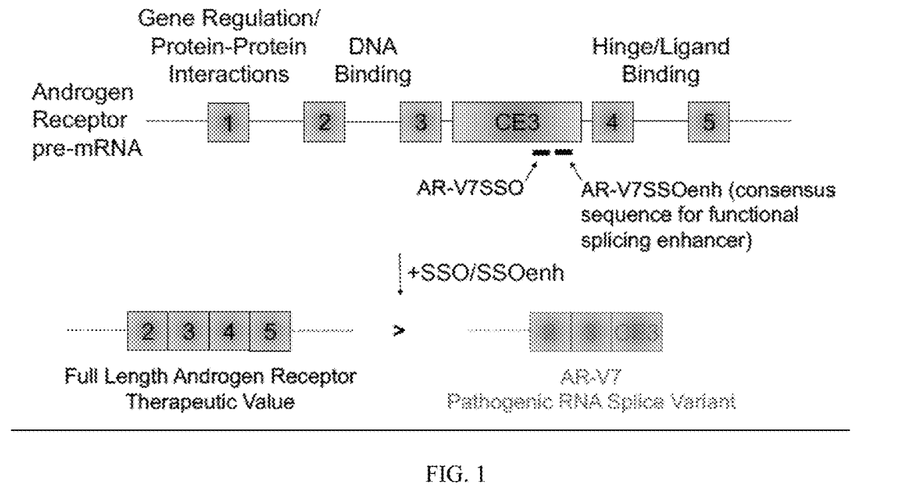
FIG. 1 is a cartoon depiction of the splice variants of AR, and the use of the anti-sense compounds (e.g. SSO/SSOenh) for reducing AR-V7 splice variant and maintaining full length Androgen receptor. SSO/AR-V7 SSO refers to ARv7 SSO-6/ARv7 SSO-6ext/ARv7 SSO-6ext (LN95 mutation)/morpholinos and AR-V7SSOenh refers to Arv7 Cons1.
Figure 2:
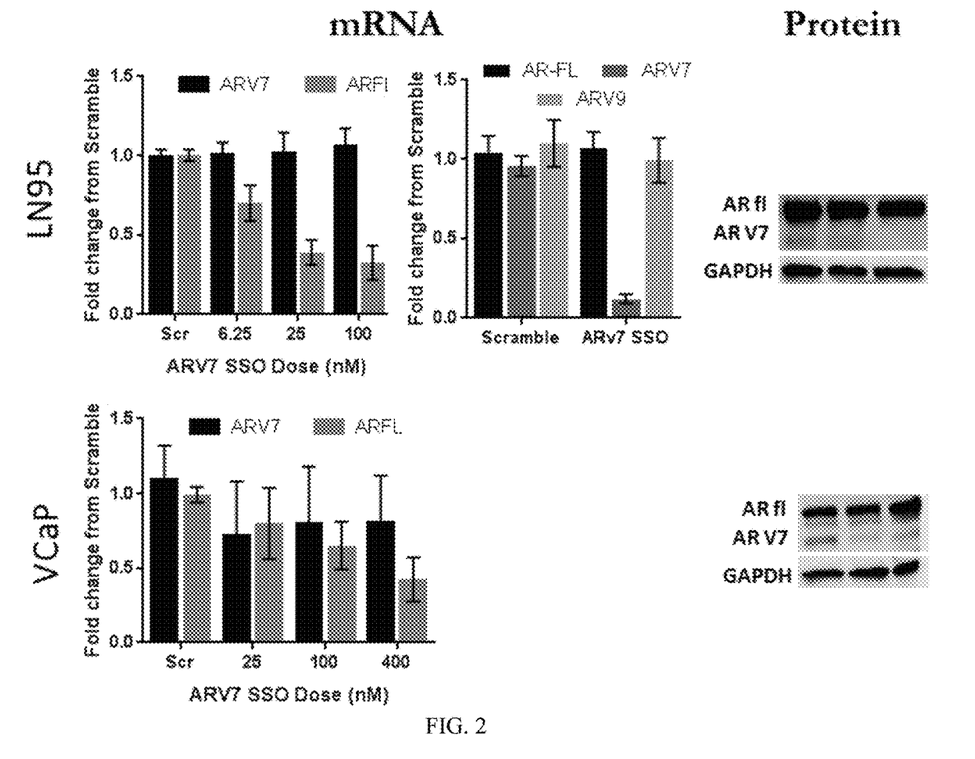
FIG. 2 depicts results of transfection of prostate cancer cell lines (as indicated) with ARv7 SSO-6 (compared with the Scramble/Scr control oligonucleotide) demonstrating a dose dependent decrease in ARv7 and maintenance of full length AR and ARv9.

Prostate cancer cells transfected with ARv7 SSO-6 (compared with the Scramble/Scr control oligonucleotide) demonstrated a dose dependent decrease in ARv7 and maintenance of full length AR and ARv9 (FIG. 2). Further, transfection of a prostate cancer cell line (LN95) with ARv7 SSO-6ext (compared with the Scramble/Scr control oligonucleotide) demonstrated a decrease in ARv7 in these cells (FIG. 3).

Figure 3:
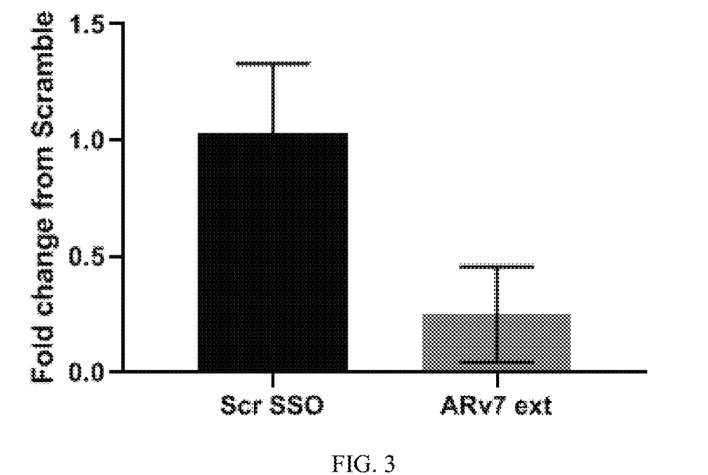
FIG. 3 demonstrates results of transfection of a prostate cancer cell line (LN95) with ARv7 SSO-6ext (compared with the Scramble/Scr control oligonucleotide) demonstrating a decrease in ARv7.

For FIGS. 2 and 3, the experimental methods is described briefly. A total of 6.25, 25, 100, or 400 nM of ARv7 SSO-6, 100 nM of ARv7 SSO-6ext, or 100 or 400 nM of Scrambled SSO was diluted in Opti-MEM and mixed with 2 uL Dharmafect 1 (LN95) or RNAiMax (VCaP) diluted in Opti-MEM for a total of 200 uL. The SSO-transfection reagent mixtures were incubated for 10 minutes at room temperature followed by plating in a 12 well plate. A total of 250,000 cells diluted in 800 uL Optimem were seeded atop the SSO-transfection reagent mixtures and incubated for 4 hours at 37° C. and 5% $CO_2$ in a humidified incubator. Media was replaced with complete media after 4 hours (RPMI+10% charcoal stripped FBS for LN95 cells and DMEM+10% FBS for VCaP cells). After an additional 72 or 96 hours of incubation, media was removed and cells were collected in RNA lysis buffer or RIPA buffer containing protease inhibitor (Thermo Fisher).

RNA was extracted using the Quick-RNA Miniprep kit (Zymo Research) following manufacturer's protocol. RNA was eluted in water and quantified using a Qubit fluorometer (Thermo Fisher). Reverse transcription (RT) reactions were performed using the ABI High Capacity cDNA Reverse Transcription Kit (Thermo Fisher) using 1 ug of RNA. RT reactions were incubated following manufacturer's protocol in a SimpliAmp thermocycler (Life Technologies). RT mixtures were diluted 1:4 in nuclease-free water and 2 uL was added to 5 uL of Kapa SYBR Fast master mix along with 1.5 uL 2 uM each forward and reverse primers for the following targets: ARv7 (ARv7_F: 5'—CCA TCT TGT CGT CTT CGG AAA TGT TAT—3' (SEQ ID NO:15) ARv7_R: 5'—TTT GAA TGA GGC AAG TCA GCC TTT CT—3') (SEQ ID NO:16), AR full length (ARfl_F: 5'—GCC TTG CTC TCT AGC CTC AA—3' (SEQ ID NO:17), ARfl_R: 5'—GGT CGT CCA CGT GTA AGT TG—3') (SEQ ID NO:18), TBP (TBP_F: 5'—TGA ATC TTG GTT GTA AAC TTG ACC—3' (SEQ ID NO:19), TBP_R: 5'—CTC ATG ATT ACC GCA GCA AA—3' (SEQ ID NO:20)). RT-qPCR was run on a ViiA7 Real-Time PCR System (Applied Biosystems) using the following conditions: 95° C. for 2 minutes, 40×(95 C for 1 second, 60° C. for 20 seconds). Fold Change from Scramble was calculated using the 2^-ΔΔCT method with TBP as the housekeeping gene and the Scrambled SSO as the treatment control.

Protein samples were quantified using a Bradford assay (Pierce Scientific) and 25 ug of each cell extract was mixed with SDS sample buffer and submitted to SDS-PAGE. Following electrophoretic transfer onto nitrocellulose membrane, blots were blocked using Starting Block (T20) (Thermo Fisher), incubated with antibodies for AR-N20 (Santa Cruz Biotechnology) and GAPDH (Sigma), and visualized using the Dyssey-FC imager (LI-COR) and LI-COR 680 and 800 secondary antibodies.

As shown, FIG. 2 depicts results of transfection of prostate cancer cell lines (as indicated) with ARv7 SSO-6 (compared with the Scramble/Scr control oligonucleotide) demonstrating a dose dependent decrease in ARv7 and maintenance of full length AR and ARv9. Further, FIG. 3 demonstrates results of transfection of a prostate cancer cell line (LN95) with ARv7 SSO-6ext (compared with the Scramble/Scr control oligonucleotide) demonstrating a decrease in ARv7.

Figure 4:
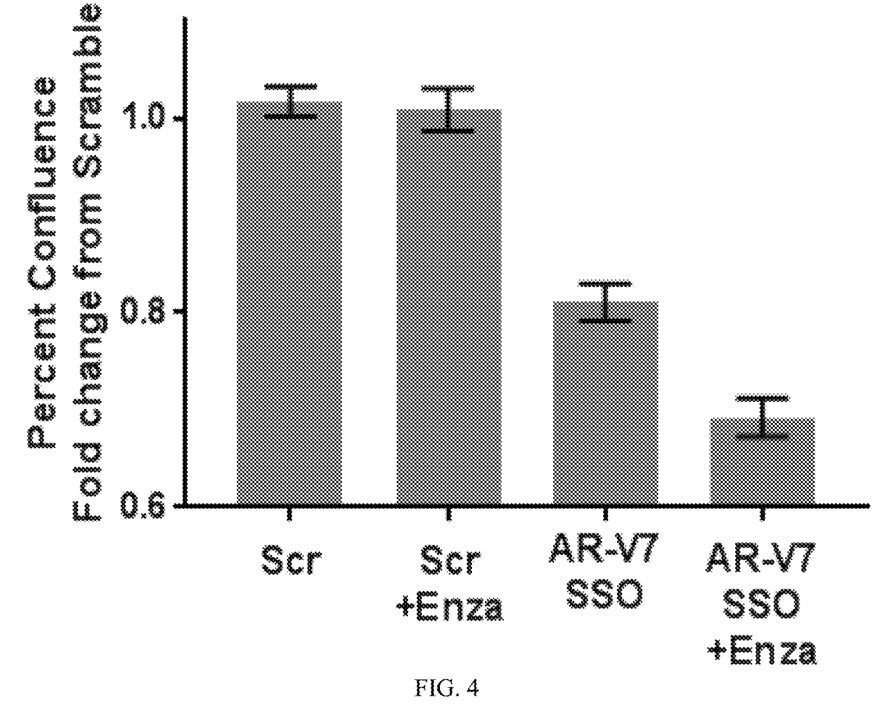
FIG. 4 demonstrates that ARv7 SSO-6 inhibits prostate cancer cell (LN95) proliferation−/+enzalutamide. Scr, control scrambled oligonucleotide.

As depicted in FIG. 4, ARv7 SSO-6 inhibits prostate cancer cell (LN95) proliferation. Briefly, a total of 100 nM of ARv7 SSO-6 or 100 nM of Scrambled SSO was diluted in Opti-MEM and mixed with 2 uL Dharmafect 1 for a total of 200 uL. The SSO-transfection reagent mixtures were incubated for 10 minutes at room temperature followed by plating in a 12 well plate. A total of 250,000 LN95 cells diluted in 800 uL Optimem were seeded atop the SSO-transfection reagent mixtures and incubated for 4 hours at 37 C and 5% $CO_2$ in a humidified incubator. Media was replaced with complete media after 4 hours (RPMI+10% charcoal stripped FBS). 72 hours later cells were lifted using 0.25% trypsin and the transfection procedure was repeated. 4 hours after transfection media was replaced with complete media and cells were gently resuspended by pipetting up and down. Cells were then seeded in to a 96 well plate at 10,000 cells/well and the plate was placed in to the Incucyte S3 live cell imager (Essen Bioscience) and incubated at 37° C. and 5% CO2 for 7 days. % confluence was calculated once per day and fold change from 0 hr was calculated for each time point.

Figure 5:
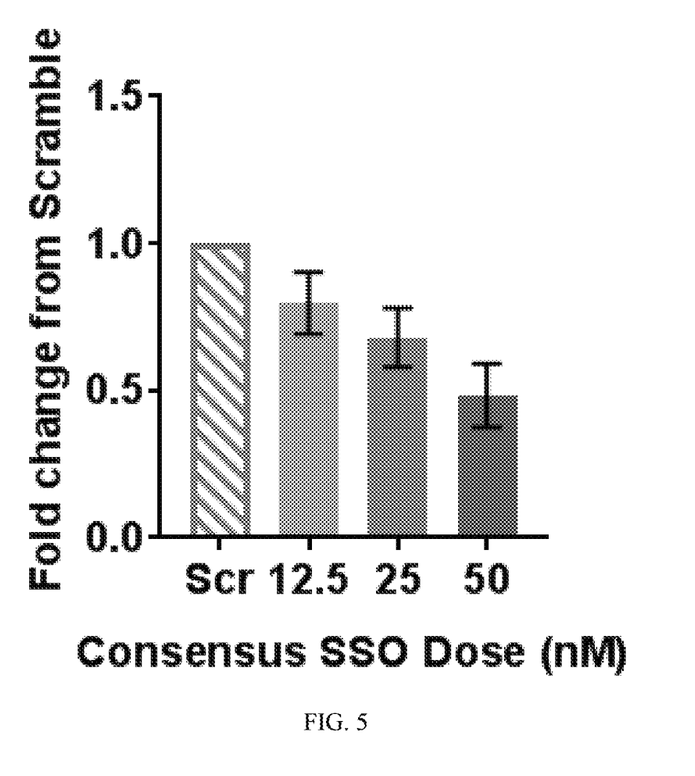
FIG. 5 demonstrates transfection of a prostate cancer cell line (LN95) with a SSO targeting a nearby consensus sequence for a functional splicing enhancer (Arv7 Cons1) decreases ARv7 RNA in a dose-dependent manner.

As depicted in FIG. 5, a SSO targeting a nearby consensus sequence for a functional splicing enhancer (Arv7 Cons1) decreases ARv7 RNA in a dose-dependent manner in LN95 prostate cancer cells. Briefly, a total of 12.5, 25, or 50 nM of ARv7 Cons1 SSO, or 50 nM of Scrambled SSO was diluted in Opti-MEM and mixed with 2 uL Dharmafect 1 diluted in Opti-MEM for a total of 200 uL. The SSO-transfection reagent mixtures were incubated for 10 minutes at room temperature followed by plating in a 12 well plate. A total of 250,000 cells diluted in 800 uL Optimem were seeded atop the SSO-transfection reagent mixtures and incubated for 4 hours at 37° C. and 5% $CO_2$ in a humidified incubator. Media was replaced with complete media after 4 hours (RPMI+10% charcoal stripped FBS). After 72 additional hours of incubation, media was removed and cells were collected in RNA lysis buffer.

RNA was extracted using the Quick-RNA Miniprep kit (Zymo Research) following manufacturer's protocol. RNA was eluted in water and quantified using a Qubit fluorometer (Thermo Fisher). Reverse transcription (RT) reactions were performed using the ABI High Capacity cDNA Reverse Transcription Kit (Thermo Fisher) using 1 ug of RNA. RT reactions were incubated following manufacturer's protocol in a SimpliAmp thermocycler (Life Technologies). RT mixtures were diluted 1:4 in nuclease-free water and 2 uL was added to 5 uL of Kapa SYBR Fast master mix along with 1.5 uL 2 uM each forward and reverse primers for the following targets: ARv7 (ARv7_F: 5'—CCA TCT TGT CGT CTT CGG AAA TGT TAT—3' (SEQ ID NO:15), ARv7_R: 5'—TTT GAA TGA GGC AAG TCA GCC TTT CT—3' (SEQ ID NO:16)), TBP (TBP_F: 5'—TGA ATC TTG GTT GTA AAC TTG ACC—3' (SEQ ID NO:19), TBP_R: 5'—CTC ATG ATT ACC GCA GCA AA—3' (SEQ ID NO:20)). RT-qPCR was run on a ViiA7 Real-Time PCR System (Applied Biosystems) using the following conditions: 95° C. for 2 minutes, 40×(95° C. for 1 second, 60° C. for 20 seconds). Fold Change from Scramble was calculated using the 2^-ΔΔCT method with TBP as the housekeeping gene and the Scrambled SSO as the treatment control.

Figure 6A:
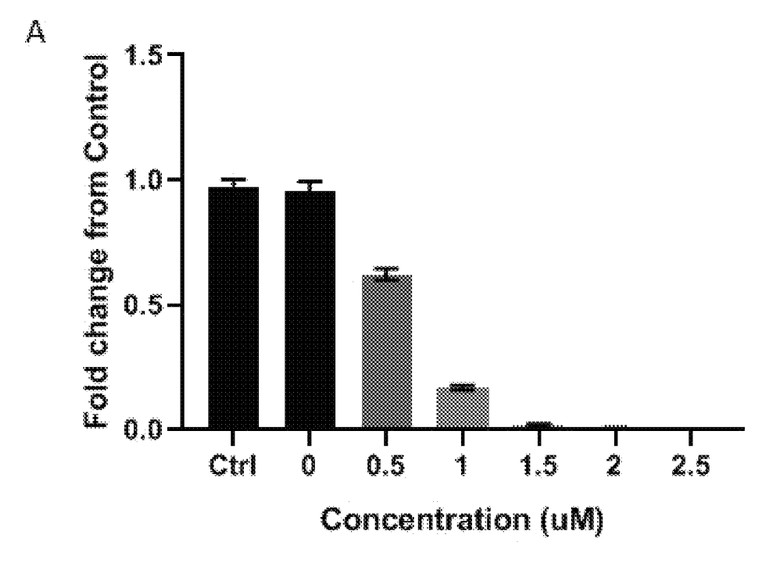
FIGS. 6A-6B depicts the results of treatment of a prostate cancer cell line (LN95) with ARv7 morph 1 showing a dose-dependent decrease in ARv7 (A) and maintenance of full length AR (B).
Figure 6B:
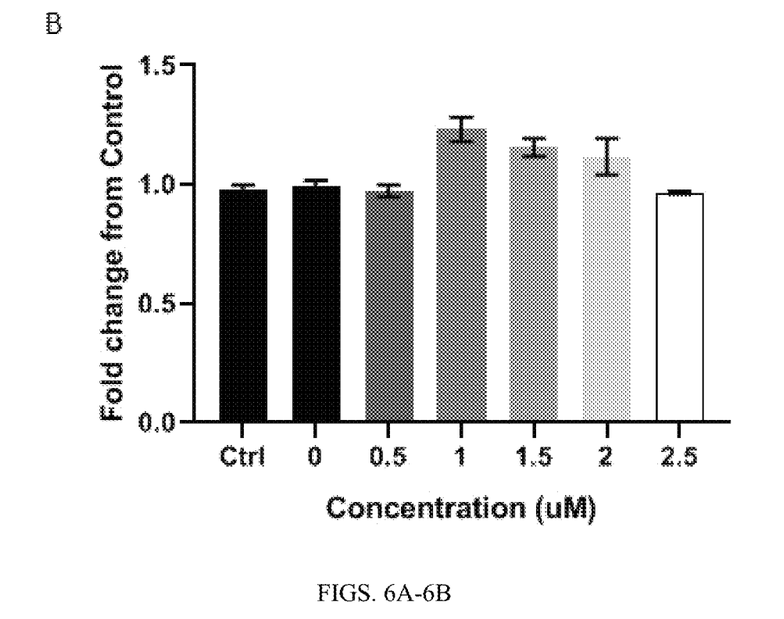

FIGS. 6A-6B demonstrate that morpholinos to Arv7 are able to decrease in a dose dependent manner Arv7 (A) and maintain full length AR (B). Briefly, LN95 cells were seeded in a 12 well plate in complete media (RPMI+10% charcoal stripped FBS) at 250,000 cells per well and incubated at 37 C and 5% $CO_2$ in a humidified incubator. After 24 hours, 0, 0.5, 1, 1.5, 2, or 2.5 uM of ARv7 morph 1 morpholino or control morpholino was diluted in complete media and added to each well. After 72 additional hours of incubation, media was removed and cells were collected in RNA lysis buffer.

RNA was extracted using the Quick-RNA Miniprep kit (Zymo Research) following manufacturer's protocol. RNA was eluted in water and quantified using a Qubit fluorometer (Thermo Fisher). Reverse transcription (RT) reactions were performed using the ABI High Capacity cDNA Reverse Transcription Kit (Thermo Fisher) using 1 ug of RNA. RT reactions were incubated following manufacturer's protocol in a SimpliAmp thermocycler (Life Technologies). RT mixtures were diluted 1:4 in nuclease-free water and 2 uL was added to 5 uL of Kapa SYBR Fast master mix along with 1.5 uL 2 uM each forward and reverse primers for the following targets: ARv7 (ARv7_F: 5'—CCA TCT TGT CGT CTT CGG AAA TGT TAT—3' (SEQ ID NO:15), ARv7_R: 5'—TTT GAA TGA GGC AAG TCA GCC TTT CT—3' (SEQ ID NO:16)), TBP (TBP_F: 5'—TGA ATC TTG GTT GTA AAC TTG ACC—3' (SEQ ID NO:19), TBP_R: 5'—CTC ATG ATT ACC GCA GCA AA—3' (SEQ ID NO:20)). RT-qPCR was run on a ViiA7 Real-Time PCR System (Applied Biosystems) using the following conditions: 95° C. for 2 minutes, 40×(95° C. for 1 second, 60° C. for 20 seconds). Fold Change from Scramble was calculated using the 2^-ΔΔCT method with TBP as the housekeeping gene and the control morpholino as the treatment control.

Thus, this data shows that SSOs consisting of sequence that is complementary to the region containing the splice site of exon CE3 reduces production of AR-V7. Morpholios to this region, e.g. SEQ ID NO: 5 (specifically for example, SEQ ID NO:12 or 14), were also synthesized that allowed for the reduction in the splice variant AR-V7. Further, the SSOs may be used in combination with androgen therapy (e.g. an antiandrogen such as enzalutamide). Dose-dependent inhibition of AR-V7 by this SSO targeting the CE3 exon corrects aberrant splicing and leads to a reduction in the production of the constitutively active AR variant AR-V7 as demonstrated in this example.

Sequence Listing Statement

The application includes the sequence listing that is concurrently filed in computer readable form. This sequence listing is incorporated by reference herein.

AR gene: found at www.ncbi.nlm.nih.gov/gene?Db=gene&Cmd=DetailsSearch&Term=367

Arv7 Cons1 (Arv7-SSO-enh): mC*mA*mG*mC*mC*mT*mT*mT*mC*mT*mT*mC*mA*mG*mG*mG*mT*mC (SEQ ID NO:1) wherein m_* are modified sugar, preferably 2'-O Me phosphorotioate.

in context (sense):

(SEQ ID NO: 2)
AATTGCAAGCATCTCAAAATGACCA[GACCCTGAAGAAAGGCTG]
ACTTGCCT (SEQ ID NO: 3)
[GACCCTGAAGAAAGGCTG]-sequence in parenthesis
that SSO binds ARv7 SSO-6-mG*mC*mC*mA*mA*mC*mC*mC*mG*mG*mA*mA*mU*mU*mU*mU*mU*mC (SEQ ID NO:4) wherein m_* are modified sugar, preferably 2'-O Me phosphorotioate.

in context (sense): caacaatgtctctctttcatacta[gAAAAATTCCGGGTTGGC]AATTGCAA (SEQ ID NO:5) [gAAAAATTCCGGGTTGGC]—sequence in parenthesis that SSO bids: SEQ ID NO:6

ARv7 SSO-6ext: mG*mC*mC*mA*mA*mC*mC*mC*mG*mG*mA*mA*mU*mU*mU*mU*mU*mC*mU*mA*mG*mU (SEQ ID NO:7) wherein m_* are modified sugar, preferably 2'-O Me phosphorotioate.

in context (sense): caacaatgtctctctttcat[actagAAAAATTCCGGGTTGGC]AATTGCAA (SEQ ID NO:5) [actagAAAAATTCCGGGTTGGC]-sequence in parenthesis that SSO bids: SEQ ID NO:8

ARv7 SSO-6ext (LN95 mutation): mG*mC*mC*mA*mA*mC*mC*mC*mG*mG*mA*mA*mU*mU*mU*mU*mU*mC* mU*mA*mG*mA (SEQ ID NO:9) wherein m_* are modified sugar, preferably 2'-O Me phosphorotioate.

in context (sense): caacaatgtctctctttcat[tctagAAAAATTCCGGGTTGGC]AATTGCAA (SEQ ID NO:5) [tctagAAAAATTCCGGGTTGGC] sequence in parenthesis that SSO bids: SEQ ID NO:10 ARv7 morph 1: TTGCCAACCCGGAATTTTTCTAGTATGA (SEQ ID NO:11)—wherein the nucleosides are morpholinos in context (sense): caacaatgtctctctt[tcatactagAAAAATTCCGGGTTGGCAA]TTGCAA (SEQ ID NO:5)—[tcatactagAAAAATTCCGGGTTGGCAA]—sequence in parenthesis that morpholino SSO bids: SEQ ID NO:12

ARv7 morph 1 (LN95 mutation): TTGCCAACCCGGAATTTTTCTAGAATGA (SEQ ID NO:13)

in context (sense): caacaatgtctctctt[tcattctagAAAAATTCCGGGTTGGCAA]TTGCAA (SEQ ID NO:5) [tcattctagAAAAATTCCGGGTTGGCAA]—sequence in parenthesis that morpholino SSO bids: SEQ ID NO:14

The invention claimed is:

1. An anti-sense compound comprising a modified splice-switching oligonucleotide (SSO) consisting of 22 to 30 linked nucleosides and having a nucleobase sequence at least 80% complementary to the corresponding nucleotide sequence within SEQ ID NO:5, wherein the SSO comprises a sequence selected from the group consisting of SEQ ID NO:7, SEQ ID NO:9, SEQ ID NO: 11 and SEQ ID NO: 13, and a sequence with at least 80% identity to SEQ ID NO:7, SEQ ID NO:9, SEQ ID NO: 11 or SEQ ID NO: 13, wherein each nucleoside of the SSO comprises a sugar modification.

2. The anti-sense compound of claim 1, wherein the sugar modification is a 2'-O-Me phosphorothioate backbone or wherein said oligonucleotide is a morpholino oligomer.

3. The anti-sense compound of claim 1, wherein the SSO consists of a nucleobase sequence complementary to the nucleotide sequence selected from the group consisting of SEQ ID NO:12, SEQ ID NO:14 and a sequence with at least 80% identity to SEQ ID NO:12 or SEQ ID NO:14, and wherein said oligonucleotide is a Morpholino oligomer.

4. The anti-sense compound of claim 1, wherein said oligonucleotide comprises a morpholino modification.

5. A composition comprising the anti-sense compound of claim 1.

6. A method of treating a subject suffering from prostate cancer comprising administering to the subject a therapeutically effective amount of a compound of claim 1, wherein the prostate cancer is treated.

7. The method of claim 6, wherein the subject has prostate cancer that is non-responsive to androgen therapy or is castrate-resistant prostate cancer.

8. The method of claim 6, wherein the subject is a human.

9. The method of claim 6, wherein the subject is an African American male suffering from prostate cancer.

10. The method of claim 6, wherein the method further comprises administering to the subject a second cancer therapy.

11. The method of claim 10, wherein the second cancer therapy is selected from the group consisting of chemotherapy, hormone therapy, androgen therapy, radiation, surgery, vaccine therapy and combinations thereof.

12. The method of claim 10, wherein the second cancer therapy is androgen therapy.

13. The method of claim 11, wherein the androgen therapy is enzalutamide.

14. A kit for treating prostate cancer comprising at least one splice-switching oligonucleotide (SSO) as set forth in claim 1.

15. The anti-sense compound of claim 1, wherein said the SSO is SEQ ID NO:11 and comprises a morpholino modification.

16. The anti-sense compound of claim 1, wherein said the SSO is SEQ ID NO:13 and comprises a morpholino modification.

17. The anti-sense compound of claim 15, wherein said SSO is a Morpholino oligomer.

18. The anti-sense compound of claim 16, wherein said SSO is a Morpholino oligomer.

19. A composition comprising the anti-sense compound of claim 17.

20. A composition comprising the anti-sense compound of claim 18.

21. A kit for treating prostate cancer comprising a splice-switching oligonucleotide (SSO) as set forth in claim 17.

22. A kit for treating prostate cancer comprising a splice-switching oligonucleotide (SSO) as set forth in claim 18.

* * * * *

SEQUENCE LISTING

```
<160> NUMBER OF SEQ ID NOS: 20

<210> SEQ ID NO 1
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(18)
<223> OTHER INFORMATION: modified sugar, preferably to 2'-O Me
      phosphorotioate

<400> SEQUENCE: 1
```
cagcctttct tcagggtc                                                18

<210> SEQ ID NO 2
<211> LENGTH: 51
<212> TYPE: DNA
<213> ORGANISM: Artificial Sequence
<220> FEATURE:
<223> OTHER INFORMATION: synthetic

<400> SEQUENCE: 2
aattgcaagc atctcaaaat gaccagaccc tgaagaaagg ctgacttgcc t            51

<210> SEQ ID NO 3
<211> LENGTH: 18
<212> TYPE: DNA
<213> ORGANISM: Artificial Sequence
<220> FEATURE:
<223> OTHER INFORMATION: synthetic

<400> SEQUENCE: 3
gaccctgaag aaaggctg                                                18

<210> SEQ ID NO 4
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(18)
<223> OTHER INFORMATION: modified sugar, preferably to 2'-O Me
      phosphorotioate

<400> SEQUENCE: 4
gccaacccgg aauuuuuc                                                18

<210> SEQ ID NO 5
<211> LENGTH: 50
<212> TYPE: DNA
<213> ORGANISM: Artificial Sequence
<220> FEATURE:
<223> OTHER INFORMATION: synthetic

<400> SEQUENCE: 5
caacaatgtc tctctttcat actagaaaaa ttccgggttg gcaattgcaa             50

<210> SEQ ID NO 6
<211> LENGTH: 18
<212> TYPE: DNA
<213> ORGANISM: Artificial Sequence
<220> FEATURE:
<223> OTHER INFORMATION: synthetic

<400> SEQUENCE: 6
gaaaaattcc gggttggc                                                18

<210> SEQ ID NO 7
<211> LENGTH: 22
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(22)
<223> OTHER INFORMATION: modified sugar, preferably to 2'-O Me
      phosphorotioate

<400> SEQUENCE: 7
gccaacccgg aauuuuucua gu                                            22

<210> SEQ ID NO 8
<211> LENGTH: 22
<212> TYPE: DNA
<213> ORGANISM: Artificial Sequence
<220> FEATURE:
<223> OTHER INFORMATION: synthetic

<400> SEQUENCE: 8
actagaaaaa ttccggggttg gc                                           22

<210> SEQ ID NO 9
<211> LENGTH: 22
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(22)
<223> OTHER INFORMATION: modified sugar, preferably to 2'-O Me
      phosphorotioate

<400> SEQUENCE: 9
gccaacccgg aauuuuucua ga                                            22

<210> SEQ ID NO 10
<211> LENGTH: 22
<212> TYPE: DNA
<213> ORGANISM: Artificial Sequence
<220> FEATURE:
<223> OTHER INFORMATION: synthetic

<400> SEQUENCE: 10
tctagaaaaa ttccgggttg gc                                            22

<210> SEQ ID NO 11
<211> LENGTH: 28
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(28)
<223> OTHER INFORMATION: Morpholino or methylenemorpholine rings linked
      through phosphorodiamidate groups

<400> SEQUENCE: 11
ttgccaaccc ggaatttttc tagtatga                                      28

<210> SEQ ID NO 12
<211> LENGTH: 28
<212> TYPE: DNA
<213> ORGANISM: Artificial Sequence
<220> FEATURE:
<223> OTHER INFORMATION: synthetic

<400> SEQUENCE: 12
tcatactaga aaaattccgg gttggcaa                                      28

<210> SEQ ID NO 13
<211> LENGTH: 28
<212> TYPE: DNA

```
<213> ORGANISM: Artificial Sequence
<220> FEATURE:
<223> OTHER INFORMATION: synthetic
<220> FEATURE:
<221> NAME/KEY: modified_base
<222> LOCATION: (1)..(28)
<223> OTHER INFORMATION: Morpholino or methylenemorpholine rings linked
      through phosphorodiamidate groups

<400> SEQUENCE: 13
ttgccaaccc ggaattttc tagaatga                                          28

<210> SEQ ID NO 14
<211> LENGTH: 28
<212> TYPE: DNA
<213> ORGANISM: Artificial Sequence
<220> FEATURE:
<223> OTHER INFORMATION: synthetic

<400> SEQUENCE: 14
tcattctaga aaaattccgg gttggcaa                                          28

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
ccatcttgtc gtcttcggaa atgttat                                           27

<210> SEQ ID NO 16
<211> LENGTH: 26
<212> TYPE: DNA
<213> ORGANISM: Artificial Sequence
<220> FEATURE:
<223> OTHER INFORMATION: synthetic

<400> SEQUENCE: 16
tttgaatgag gcaagtcagc ctttct                                            26

<210> SEQ ID NO 17
<211> LENGTH: 20
<212> TYPE: DNA
<213> ORGANISM: Artificial Sequence
<220> FEATURE:
<223> OTHER INFORMATION: synthetic

<400> SEQUENCE: 17
gccttgctct ctagcctcaa                                                   20

<210> SEQ ID NO 18
<211> LENGTH: 20
<212> TYPE: DNA
<213> ORGANISM: Artificial Sequence
<220> FEATURE:
<223> OTHER INFORMATION: synthetic

<400> SEQUENCE: 18
ggtcgtccac gtgtaagttg                                                   20

<210> SEQ ID NO 19
<211> LENGTH: 24
<212> TYPE: DNA
<213> ORGANISM: Artificial Sequence
<220> FEATURE:
```

```
<223> OTHER INFORMATION: synthetic

<400> SEQUENCE: 19
tgaatcttgg ttgtaaactt gacc                                              24

<210> SEQ ID NO 20
<211> LENGTH: 20
<212> TYPE: DNA
<213> ORGANISM: Artificial Sequence
<220> FEATURE:
<223> OTHER INFORMATION: synthetic

<400> SEQUENCE: 20
ctcatgatta ccgcagcaaa                                                   20
```

UNITED STATES PATENT AND TRADEMARK OFFICE
CERTIFICATE OF CORRECTION

| | | |
|---|---|---|
| PATENT NO. | : 11,866,689 B2 | Page 1 of 1 |
| APPLICATION NO. | : 17/041843 | |
| DATED | : January 9, 2024 | |
| INVENTOR(S) | : Jennifer Freedman et al. | |

It is certified that error appears in the above-identified patent and that said Letters Patent is hereby corrected as shown below:

In the Claims

At Column 25, Claim number 3, Line number 38, please replace "Morpholino" with --morpholino--

At Column 26, Claim number 15, Line number 34, please delete "the" after "said"

At Column 26, Claim number 16, Line number 37, please delete "the" after "said"

At Column 26, Claim number 17, Line number 41, please replace "Morpholino" with --morpholino--

At Column 26, Claim number 18, Line number 43, please replace "Morpholino" with --morpholino--

Signed and Sealed this
First Day of October, 2024

Katherine Kelly Vidal
*Director of the United States Patent and Trademark Office*